United States Patent [19]

Kees, Jr.

[11] Patent Number: 4,658,822
[45] Date of Patent: Apr. 21, 1987

[54] ANEURYSM CLIP

[76] Inventor: George Kees, Jr., 104 North St., Wilder, Ky. 41071

[21] Appl. No.: 815,247

[22] Filed: Dec. 31, 1985

[51] Int. Cl.$^4$ ............................................. A61B 17/12
[52] U.S. Cl. .................................. 128/325; 128/346; 24/546
[58] Field of Search ............... 128/325, 326, 346, 354; 24/547, 551, 546, 561, 562, 566; 294/99.1

[56] References Cited

U.S. PATENT DOCUMENTS

| | | | |
|---|---|---|---|
| 2,704,071 | 3/1955 | Becker | 128/346 X |
| 3,827,438 | 8/1974 | Kees | 128/346 |
| 4,024,868 | 5/1977 | Williams | 128/325 |
| 4,444,187 | 4/1984 | Perlin | 128/325 X |

*Primary Examiner*—Michael H. Thaler
*Attorney, Agent, or Firm*—James W. Pearce; Roy F. Schaeperklaus

[57] ABSTRACT

An aneurysm clip which includes an elongated main section providing a central spring portion, jaw forming portions, and connecting portions between the central spring portion and the jaw forming portions. Return bent jaw addition sections are provided on opposite sides of the jaw forming portions of the main section. The connecting portions cross each other and each jaw forming portion of the main section is opposed to and urged toward one of the return bent jaw addition sections.

3 Claims, 9 Drawing Figures

ANEURYSM CLIP

BACKGROUND OF THE INVENTION

This invention relates to aneurysm clips. More particularly, this invention relates to an aneurysm clip of small size fabricated from a single piece of spring wire and having double-width jaws.

An object of this invention is to provide an aneurysm clip of small size which represents an improvement in the type of clip shown and claimed in applicant's U.S. Pat. No. 3,827,438.

SUMMARY OF THE INVENTION

Briefly, this invention provides an aneurysm clip formed from a single length of spring wire, end sections of which are return bent to form jaw addition sections on opposite sides of end portions of the main section. A central portion of the main section of the clip forms a spring. The jaw addition sections and the end portions of the main section form cooperating clamping jaws which are connected to the spring portion by connecting portions.

The above and other objects and features of the invention will be apparent to those skilled in the art to which this invention pertains from the following detailed description and the drawings, in which:

DESCRIPTION OF PRESENTLY PREFERRED EMBODIMENT

Figure 1:
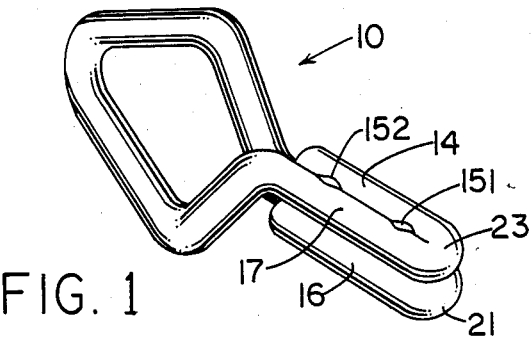
FIG. 1 is a perspective view of an aneurysm clip constructed in accordance with an embodiment of this invention.

In the following detailed description and the drawing, like reference characters indicate like parts.

Figure 8:
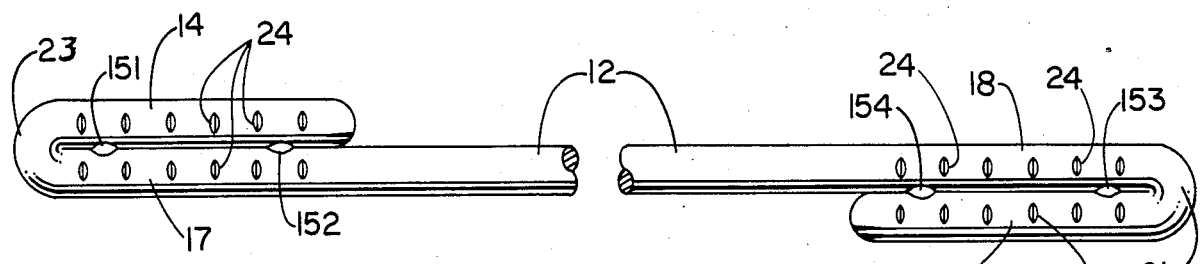
FIG. 8 is a plan view of a blank assembly from which the aneurysm clip is formed, in partly formed condition.
Figure 9:
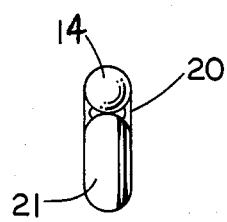
FIG. 9 is a view in end elevation of the partly formed blank assembly.

In FIGS. 1-7 inclusive is shown an aneurysm clip 10 constructed in accordance with an embodiment of this invention. The clip 10 is formed from an elongated length of spring metal (FIGS. 8 and 9) of circular cross section. Clip 10 includes a main section 12 and two short end sections 14 and 16. The short end sections 14 and 16 are oppositely bent to lie on opposite sides of the main section 12 in parallel coplanar relation to each other and the main section 12, as shown in FIGS. 8 and 9. The short end sections 14 and 16 are substantially in face-to-face relation with the end portions 17 and 18 of the main section 12. The short end sections 14 and 16 are respectively rigidly attached to the end portions 17 and 18 of the main section 12 by return bend portions 21, 23 and by welds 151, 152, 153, 154 to form jaws 20 and 22. Each jaw has a central longitudinal groove bounded on its sides by a respective short end section 14, 16 and a respective end portion 17, 18 and at the free end of the jaw by a respective return bend 21, 23. Transverse slots 24 are formed in faces of the jaws 20 and 22 to improve the non-slip character thereof.

Figure 2:
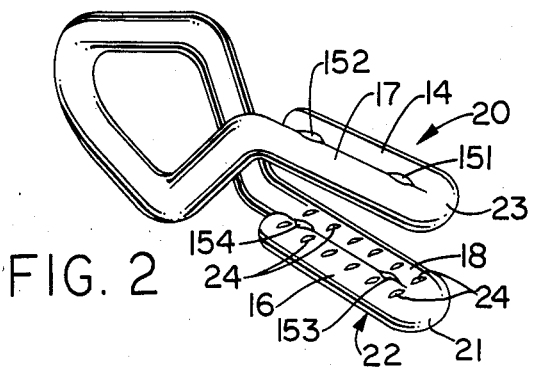
FIG. 2 is a perspective view of the aneurysm clip in open position.
Figure 3:
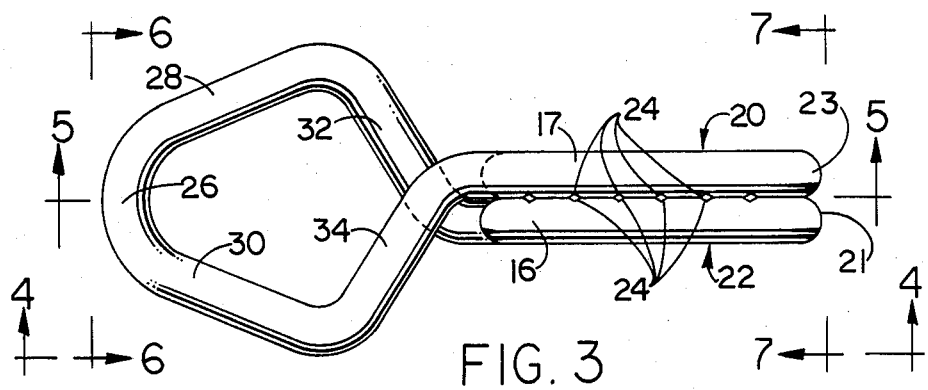
FIG. 3 is a plan view of the aneurysm clip.
Figure 4:
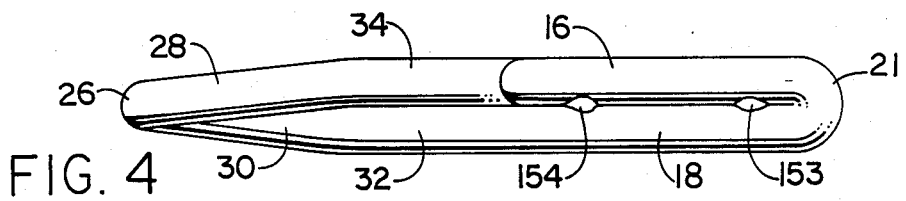
FIG. 4 is a view in side elevation of the aneurysm clip, looking in the direction of the arrows 4—4 in FIG. 3.
Figure 5:
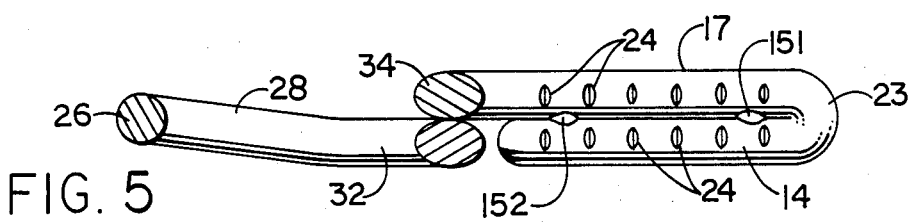
FIG. 5 is a view in section taken on the line 5—5 in FIG. 3.
Figure 6:
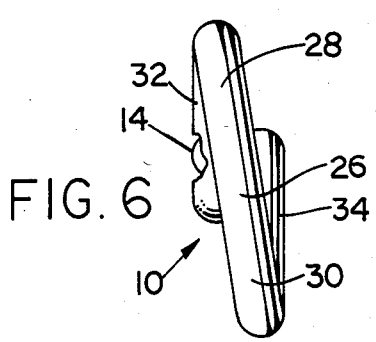
FIG. 6 is a view in end elevation of the clip looking in the direction of the arrows 6—6 in FIG. 3.
Figure 7:
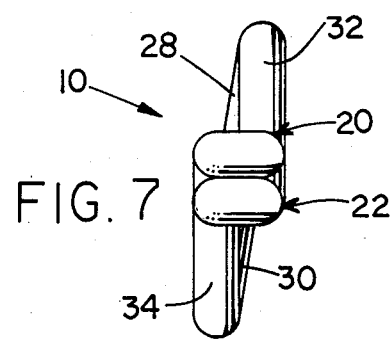
FIG. 7 is a view in end elevation of the aneurysm clip looking in the direction of the arrows 7—7 in FIG. 3.

The main section 12 is formed to a central spring section 26, diverging first connecting portions 28 and 30 integrally formed with and connected by the central spring section 26 and converging second connecting portions 32 and 34, which connect the first connecting portions 28 and 30 to the jaws 22 and 20, respectively. The second connecting portions cross as shown in FIGS. 1, 2 and 3. When the clip 10 is in closed position, as shown in FIG. 1, the end portion 17 of the main section 12 overlies the short end section 16, the end portion 18 of the main section 12 underlies the short end section 14 and return bent section 23 overlies return bent section 21. The end portions 17 and 18 of the main section 12 are parallel to each other but are spaced when the clip is in the closed position shown in FIGS. 1 and 7.

The clip 10 can be manipulated and opened by means of an appropriate tool (not shown) such as one of the tools shown in my U.S. Pat. Nos. 2,876,778 and 3,827,438, or my copending application Ser. No. 6/815,388 filed Dec. 31, 1985. The open clip can be positioned to close on an aneurysm (not shown) and can be released to seal off the aneurysm.

Having described my invention, what I claim as new and desire to secure by Letters Patent is:

1. An aneurysm clip which comprises an elongated main section of spring metal and a pair of short length jaw addition sections attached to end portions of the main section on opposite sides of the main section, the main section being formed to a central spring portion, diverging first connecting portions extending from the central spring portion, converging second connecting portions extending from the first connecting portions, and jaw end portions extending from the second converging second connecting portions, one second connecting portion and associated jaw end portion being coplanar with and adjacent a respective first side of a plane parallel to jaw movement, the other connecting portion and associated jaw end portion being coplanar with and adjacent a respective second side of said plane parallel to jaw movement, each associated short length jaw addition being on the opposite side of said plane from the jaw end portion to which it is attached, the jaw end portions being arranged so that each of the jaw end portions is opposed to one of the short length jaw addition sections, the central spring section urging the jaw end portions toward engaged position with the jaw addition sections.

2. An aneurysm clip as in claim 1 in which the second connecting portions cross and the jaw end portions of the main section are parallel to each other when in a closed position.

3. An aneurysm clip as in claim 1 in which the main section and the short length jaw addition sections are of substantially circular cross section.

* * * * *